United States Patent
Yan et al.

(10) Patent No.: US 11,957,936 B2
(45) Date of Patent: Apr. 16, 2024

(54) PASSIVE WIRE REFLECTORS FOR IMPROVED IMAGE QUALITY IN MR-GUIDED FOCUSED ULTRASOUND

(71) Applicant: Vanderbilt University, Nashville, TN (US)

(72) Inventors: Xinqiang Yan, Nashville, TN (US); William A. Grissom, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/931,370

(22) Filed: May 13, 2020

(65) Prior Publication Data

US 2020/0360733 A1    Nov. 19, 2020

Related U.S. Application Data (60) Provisional application No. 62/894,188, filed on Aug. 30, 2019, provisional application No. 62/847,748, filed on May 14, 2019.

(51) Int. Cl.
*A61B 5/055* (2006.01)
*A61B 5/00* (2006.01)
(Continued)

(52) U.S. Cl.
CPC .............. *A61N 7/02* (2013.01); *A61B 5/0036* (2018.08); *A61B 5/055* (2013.01);
(Continued)

(58) Field of Classification Search
None
See application file for complete search history.

(56) References Cited

U.S. PATENT DOCUMENTS

2013/0006106 A1* 1/2013 O'Reilly .............. A61B 8/0808
600/431
2014/0266189 A1* 9/2014 Salomir ................... A61N 7/02
324/307

(Continued)

FOREIGN PATENT DOCUMENTS

WO    WO 2019/089372    5/2019

OTHER PUBLICATIONS

Yan et al. (Improved traveling-wave efficiency in 7 T human MRI using passive local loop and dipole arrays; Magnetic Resonance Imaging 39 (2017) 103-109).*

(Continued)

*Primary Examiner* — Shahdeep Mohammed
(74) *Attorney, Agent, or Firm* — Blank Rome LLP (57) ABSTRACT

A system for transcranial magnetic resonance (MR)-guided focused ultrasound and method of using transcranial MR-guided focused ultrasound are disclosed. The system includes a transcranial ultrasound transducer configured to apply ultrasound radiation to a patient's head. The system also includes an antenna that reflects radio frequency (RF) waves. The antenna is configured to be positioned between the transducer and the patient's head. The antenna and at least a portion of the patient's head are surrounded by a fluid. Embodiments foster improved MR image quality scans of the patient's head when the transducer is filled with the fluid.

20 Claims, 6 Drawing Sheets

(51) Int. Cl.
| | |
|---|---|
| *A61N 7/00* | (2006.01) |
| *A61N 7/02* | (2006.01) |
| *G01R 33/34* | (2006.01) |
| *G01R 33/48* | (2006.01) |

(52) U.S. Cl.
CPC ... *G01R 33/34038* (2013.01); *G01R 33/4814* (2013.01); *A61N 2007/0021* (2013.01); *G06T 2207/10088* (2013.01)

(56) References Cited

U.S. PATENT DOCUMENTS

| | | | |
|---|---|---|---|
| 2018/0275234 A1 | 9/2018 | Han et al. | |
| 2019/0021666 A1* | 1/2019 | Hynynen | ............... A61B 90/14 |
| 2020/0200844 A1* | 6/2020 | Boskamp | ........... G01R 33/4215 |

OTHER PUBLICATIONS

Keil et al. ("Massively parallel MRI detector arrays"; Journal Of Magnetic Resonance 223 (2013)).*

Yan, Xinqiang, et al. "Optimization of an 8-channel loop-array coil for a 7 T MRI system with the guidance of a co-simulation approach." Applied Magnetic Resonance 45.5 (2014): 437-449.

Yan, Xinqiang, John C. Gore, and William A. Grissom. "Traveling-wave meets standing-wave: A simulation study using pair-of-transverse-dipole-ring coils for adjustable longitudinal coverage in ultra-high field MRI." Concepts in Magnetic Resonance Part B: Magnetic Resonance Engineering 48.4 (2018): e21402.

Grissom, William A., et al. "Hybrid referenceless and multibaseline subtraction MR thermometry for monitoring thermal therapies in moving organs." Medical physics 37.9 (2010): 5014-5026.

Yagi, Hidetsugu. "Beam transmission of ultra short waves." Proceedings of the Institute of Radio Engineers 16.6 (1928): 715-740.

Köhler, M. O., et al. "Ultrasound-transparent RF coil design for improved MR thermometry of HIFU therapy." Proceedings of the 19th Annual Meeting of ISMRM, Montreal, Canada. 2011.

McDannold, N. "Quantitative MRI-based temperature mapping based on the proton resonant frequency shift: review of validation studies." International journal of hyperthermia 21.6 (2005): 533-546.

McDannold, Nathan, et al. "Transcranial magnetic resonance imaging—guided focused ultrasound surgery of brain tumors: initial findings in 3 patients." Neurosurgery 66.2 (2010): 323-332.

Rieke, Viola, et al. "Referenceless PRF shift thermometry." Magnetic Resonance in Medicine: An Official Journal of the International Society for Magnetic Resonance in Medicine51.6 (2004): 1223-1231.

Holbrook, Andrew B., et al. "Real-time MR thermometry for monitoring HIFU ablations of the liver." Magnetic Resonance in Medicine: An Official Journal of the International Society for Magnetic Resonance in Medicine 63.2 (2010): 365-373.

Haines, K., N. B. Smith, and A. G. Webb. "New high dielectric constant materials for tailoring the B1+ distribution at high magnetic fields." Journal of magnetic resonance 203.2 (2010): 323-327.

Butts Pauly, Kim., et al. "RF Shimming in an MRgFUS Brain Transducer with a High Permittivity Material". ISMRM (2014) p. 2331.

Leung, Steve, Pejman Ghanouni, and Kim Butts Pauly. "Reduction of dielectric artifacts within an InSightec ExAblate 4000 head transducer." Journal of therapeutic ultrasound 3.1 (2015): P27.

Focused Ultrasound Foundation. Brain Program's mini-workshop called "a landmark example" of academic-industrial collaboration. Aug. 2012. https://www.fusfoundation.org/Newsletter-Articles/brain-programs-mini-workshop-called-a-landmark-example-of-academic-industrial-collaboration.

Horch, R. Adam, and John C. Gore. "3D-printed RF probeheads for low-cost, high-throughput NMR." ISMRM (2017) p. 2147.

* cited by examiner

PASSIVE WIRE REFLECTORS FOR IMPROVED IMAGE QUALITY IN
MR-GUIDED FOCUSED ULTRASOUND

CROSS REFERENCE TO RELATED APPLICATION(S)

This application claims priority to U.S. provisional patent application number 62/847,748, filed on May 14, 2019, and U.S. provisional patent application No. 62/894,188, filed on Aug. 30, 2019, both of which are hereby incorporated herein by reference in their entireties.

FIELD OF THE INVENTION

Embodiments are in the field of systems and methods for imaging. More particularly, embodiments disclosed herein relate to systems and methods for improving image quality in magnetic resonance (MR)-guided focused ultrasound.

BACKGROUND OF THE INVENTION

Transcranial MR-guided focused ultrasound (tcMRgFUS) neurosurgery is a non-invasive treatment for essential tremor, neuropathic pain and many emerging applications. During treatment, magnetic resonance imaging (MRI) scans are used to localize the target and monitor temperature, and the patient's head is positioned in a water bath that couples acoustic energy to the head and circulates water to cool the scalp between sonications.

Figure 1:
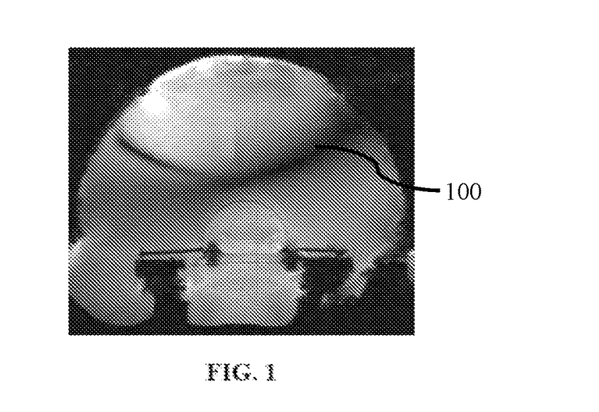
FIG. 1 is a diagram illustrating a sagittal image of a QA phantom in an INSIGHTEC° transcranial transducer which is filled with water.

A water bath is used for treatment as it acts as a high permittivity dielectric with a shorter radio frequency (RF) wavelength than free space (approximately 9× shorter). At the present time, the FDA-approved INSIGHTEC® system has a conductive transducer surface which was introduced to improve electric-to-acoustic energy conversion efficiency. Because the body coil built into the scanner housing is used for all MRI RF transmission and signal reception in tcMRgFUS, the electromagnetic waves that interact with the brain tissue for imaging must come from the bottom opening of the transducer, since they cannot pass directly through the transducer bowl. Thus, RF waves for imaging travel from the opening at the bottom of the transducer to the top, where they are reflected. Due to the geometry of the bowl, the reflected waves cancel, affect, or interfere with the incoming waves approximately one quarter-wavelength from the top of the transducer (FIG. 1). That produces a dark band 100 in the brain images near the midbrain locations that are targeted for essential tremor. Signals are also broadly reduced throughout the brain. FIG. 1 illustrates a sagittal image of a quality assurance (QA) phantom in the INSIGHTEC® transducer which is filled with water. The arrow points to the dark band 100.

To address that problem, researchers have proposed doping the water to change its electrical properties, adding dielectric pads to manipulate the bright spots of the RF field, and building new RF coils that sit inside the water bath and can transmit directly into the tissue with less concern for reflections from the bowl. However, dielectric pads can have only limited success in manipulating the field or can only improve it in one focal location, since they do not address the fundamental problem. New RF coils are complicated by the need to route electrical energy safely into the water bath, and the potential ultrasound disturbances they would produce. There are also significant challenges associated with doping the water, since a solution must be found that is non-toxic, does not modify the speed of sound, can be circulated while maintaining the water's capacity for removing heat from the skull, does not lower the acoustic cavitation threshold, is not corrosive, and can be obtained in the large volumes required to fill the transducer and cooling and degassing circuits.

Thus, it is desirable to provide a system and method for improving image quality in MR-guided focused ultrasound that is able to overcome the above disadvantages.

Advantages of the present invention will become more fully apparent from the detailed description of the invention hereinbelow.

SUMMARY OF THE INVENTION

Embodiments are directed to a system for transcranial MR-guided focused ultrasound. The system includes a transcranial ultrasound transducer configured to apply ultrasound radiation to a patient's head. The system also includes an antenna that reflects RF waves. The antenna is configured to be positioned between the transducer and the patient's head.

Embodiments are also directed to a method of using transcranial MR-guided focused ultrasound. The method includes applying ultrasound radiation to a patient's head using a transcranial ultrasound transducer. The method also includes reflecting RF waves using an antenna positioned between the transducer and the patient's head.

Additional embodiments and additional features of embodiments for the system for transcranial MR-guided focused ultrasound and method of using transcranial MR-guided focused ultrasound are described below and are hereby incorporated into this section.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It is understood, however, that the inventive concepts disclosed herein are not limited to the precise arrangements and instrumentalities shown in the FIGS. The detailed description will refer to the following drawings in which like numerals, where present, refer to like items.

DETAILED DESCRIPTION OF THE INVENTION

It is to be understood that the FIGS. and descriptions of the present invention may have been simplified to illustrate elements that are relevant for a clear understanding of the present invention, while eliminating, for purposes of clarity, other elements found in a typical system for MR-guided focused ultrasound or typical methods of using or operating MR-guided focused ultrasound. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented devices, systems, methods, features, and advantages will be or become apparent to one with skill in the art upon examining the drawings and the detailed description herein. It is intended that all such additional devices, systems, methods, features, and advantages be protected by the accompanying claims.

For purposes of this disclosure, the terms "antenna", "wire", and "resonator" may all be used interchangeably.

This disclosure solves the MR image quality problems described above by developing passive antennas placed inside a water bath, above a patient's head and within a transcranial ultrasound transducer. The antennas work by reflecting the incoming RF waves coming from the bottom (i.e., open concave end) of the transducer, before those waves arrive at the transducer surface and reflect. And unlike the conductive transducer surface, the reflected signal's amplitude and phase can be tuned by varying the wires' length, position, and/or orientation/angulation. In that way, the reflected signal can be optimized so as to not cancel with the original incoming RF field, but instead to add constructively with it to increase transmit efficiency and receive sensitivity. Unlike RF coils placed in the water bath, embodiments of this disclosure do not require any external electrical connections, and the system can be made much more compact so as to minimally perturb the ultrasound beam. Unlike doping, embodiments of this disclosure will be safe for use with human subjects and will not modify the water's acoustic properties. Finally, embodiments of this disclosure could be immediately deployed on existing systems, and will be compatible with the in-bath two-channel receive-only coil that INSIGHTEC® may release for 3 Tesla imaging, which will address the low receive sensitivity problem but will not address the low transmit efficiency problem. The solutions of this disclosure addresses both. Overall, passive crossed wires are a simple low-cost solution to dramatically improve MR image quality during tcMRgFUS procedures.

In other words, in tcMRgFUS neurosurgery, the patient's head is placed in a water bath that couples acoustic energy to the head and circulates water to cool the scalp between sonications. The water acts as a high permittivity dielectric and induces artifacts in MRI, especially when the surface of the transducer is conductive. This RF inhomogeneity results in dielectric artifacts that appear as dark regions in the MR images, positioned approximately a quarter wavelength from the transducer's inner surface, and the MR signal is reduced everywhere in the brain, which prevents the use of all but a few MR sequences when the transducer is filled with water. To solve this problem, the present disclosure proposes a novel system and method to eliminate the artifacts using passive antennas placed inside the water bath, above the patient's head. One implementation of this idea is to place a pair of orthogonal dipole antennas/crossed wires above the patient's head. Broadly, a passive dipole antenna acts as a reflector in traveling wave MRI.

Figure 2:
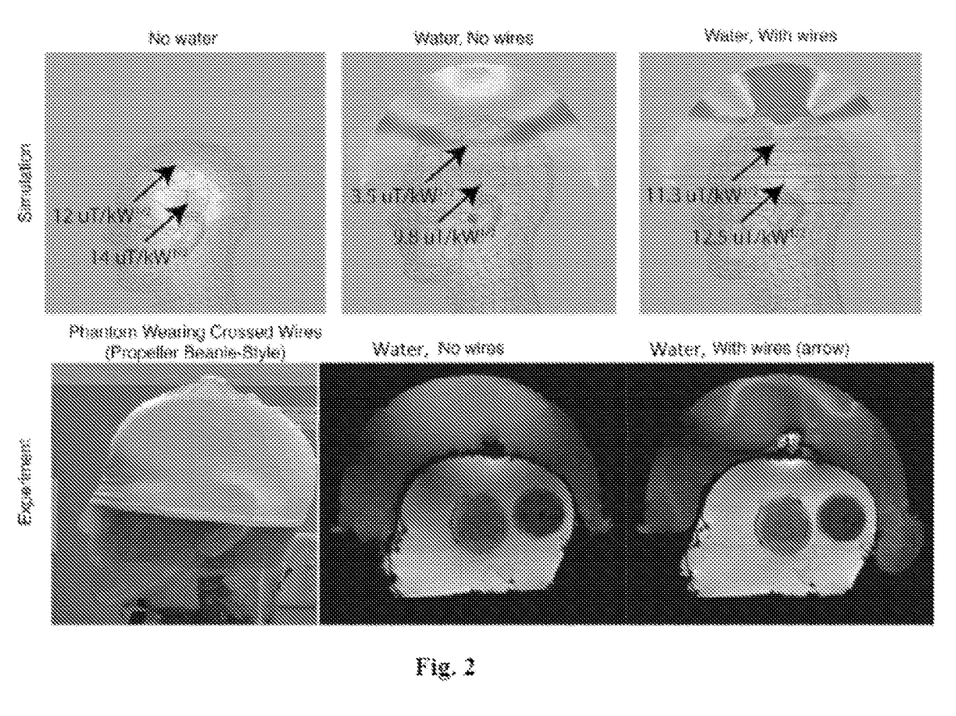
FIG. 2 is a diagram illustrating a sagittal simulation (top row) and experimental results (bottom row) without and with passive crossed wires.

The present disclosure describes simulations and an experiment to demonstrate the potential of the passive crossed wires (FIG. 2). FIG. 2 is a diagram illustrating a sagittal simulation (top row) and experimental (bottom row) results without and with passive crossed wires. In FIG. 2, the simulations in the top row show that the RF transmit field is nearly completely canceled in a wide band through the brain due to the presence of the water and transducer (top left vs. top middle). The top left image shows a map of transmit efficiency without the transducer or water bath, which has a bright spot in it that is characteristic of volume coil imaging at 3 Tesla. The top middle image shows how the transmit efficiency is nearly completely canceled due to cancelation between the incoming RF wave coming from the RF coil, and the outgoing RF wave reflected off the inner surface of the transducer. The top right image shows that by adding a pair of crossed wires above the head with lengths of 12 cm, the dark band is removed and most of the transmit efficiency is recovered. The bottom left photo shows a head phantom wearing a swim cap that has a pair of crossed wires attached. This phantom was placed in the INSIGHTEC® transducer and imaged without the wires (middle bottom image), which illustrates the signal loss in the dark band. With the wires (right bottom image), the dark band is removed and the signal is brighter throughout the phantom, similar to the simulations. Note that these improvements were achieved without optimizing the wire lengths, their position or angulation.

In a more detailed explanation of FIG. 2, the top row shows the magnitude of the RF transmit efficiency ($B_1+$) with no water, with water but with no wires, and with water and 12 cm crossed wires. Specific magnitudes in the midbrain and in the dark band region are reported in each case. The left bottom row shows a head phantom wearing a swim cap with a pair of 12 cm crossed wires attached exteriorly at the top (propeller beanie-style). The middle bottom row shows a gradient-recalled echo (GRE) image of the phantom without the wires, which contains the dark band. The right bottom row shows an image of the phantom with the crossed wires, which alleviated the dark band. The bottom row (middle and right) are with water.

Embodiments of this disclosure describe employing passive crossed wire antennas that can be immediately used for human subjects to improve MR image quality inside the transducer with the water-filled bath (or other fluid). The ultrasound transducer may operate at, for example, 650 kHz. Embodiments of this disclosure serve to:

1) Optimize the antennas to maximize signal recovery while ensuring safety. Electromagnetic simulations are used in male and female head models in multiple transducer-head positions to optimize the lengths, positions, and orientations of the wires. Maximum local and head-averaged specific absorption rate (SAR) will be computed for each configuration, to make sure that the wires will not cause unsafe heating in the upper brain.
2) Produce a mechanical holder for the wires, and a method to manufacture it by 3D printing or other suitable processes. The holder will have legs that reach down along the inner seams of the transducer, to anchor it to the outer transducer rim, where it can be attached to the ring of the membrane or held down by it. At the optimal depth in the transducer, the legs will jump across the bath in straight segments that hold the antenna wires/conductors.
3) Evaluate improvements in signal-to-noise ratio (SNR) and transmit efficiency and validate that hot spots are not distorted. SNR improvement of GRE and spin echo images are achieved in healthy volunteers with the wires.

Optimization of the Antennas to Maximize Signal Recovery, and Perform Safety Modeling.

Figure 3:
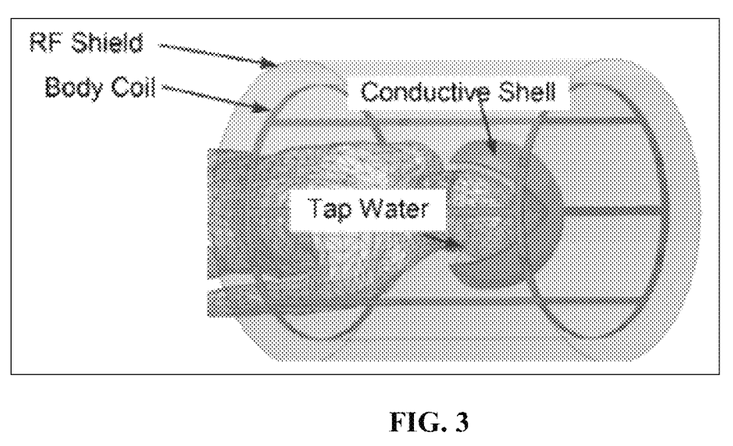
FIG. 3 is a diagram illustrating a simulation setup. The transcranial transducer is modeled as a conductive shell containing tap water and the head. The body, including the head, is surrounded by the MRI scanner's birdcage body coil.

The lengths, positions, and/or orientations/angulations of the two wires are optimized to maximize the RF transmit and receive fields in the brain. To find a robust design across head sizes and positions with respect to the transducer, male and female head models at multiple positions will be simulated using the same full-wave electromagnetic simulation software and the body coil RF circuit co-simulation method that was used in FIG. 2. The zoomed-out simulation setup is illustrated in FIG. 3. The transcranial transducer is modeled as a conductive shell containing tap water and the head. In other words, the conductive shell represents a portion of an ultrasound transducer. The body, including the head, is surrounded by the MRI scanner's birdcage body coil. The RF shield and body coil represent portions of an MR scanner.

Figure 4A:
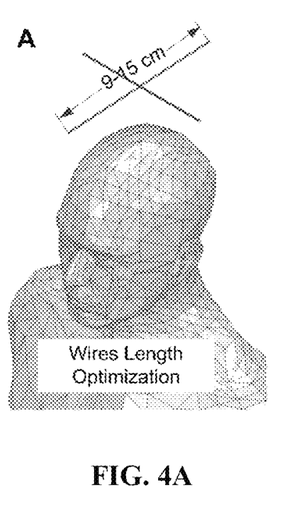
FIGS. 4A-4C are diagrams respectively illustrating optimization variables: the wires' lengths, position above the head, and orientation/angle with respect to the head.
Figure 4B:
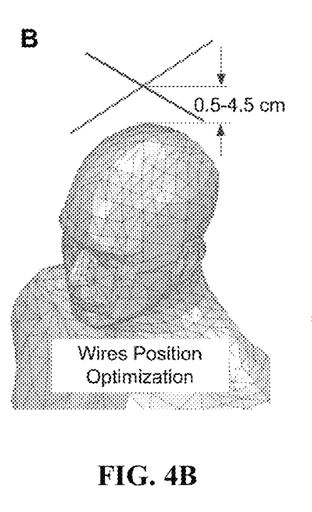
Figure 4C:
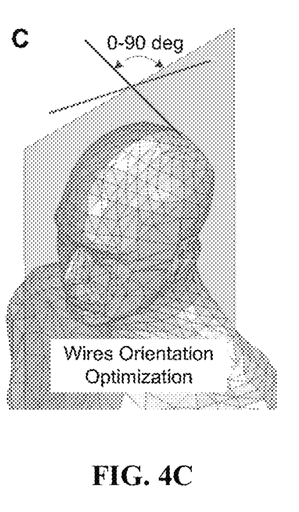

FIG. 4 shows a diagram illustrating optimization variables: the wires' lengths, position above the head, and orientation/angle with respect to the head. With an electrical length of ($\lambda/2*n$) where n is an integer, an open wire is a dipole antenna that can reflect the RF wave coming into the transducer bowl from the body coil, and the magnitude and phase of the reflected wave can be adjusted by slightly varying the dipole's length. When immersed in the high-permittivity water ($\varepsilon_r=80$), a half-wavelength dipole is approximately 12 cm long. This length will be the midpoint of an optimization, and lengths between 9 cm and 15 cm may be considered (FIG. 4A). The height of the wires above the head (FIG. 4B) will also be optimized, or equivalently the distance between the wires and the top of the bowl. A height of the wires above the head may be between 0.5 and 4.5 cm. A closer wire-to-head distance providing greater $B_1$ correction will be expected but may induce higher E-field and consequently higher SAR. Unfeasible wire length and position combinations that intersect the bowl will be excluded. Finally, the orientation/angle of the wires with respect to the sagittal plane of the head will be optimized (FIG. 4C), and an angle of a wire of between 0 and 90 degrees with respect to the sagittal plane of the head may be employed. As shown, in the case of two wires, they may be positioned 90° with respect to each other. Likewise, three wires may be positioned 60° from each other. A higher number of wires may be equally radially distributed as well.

Figure 5:
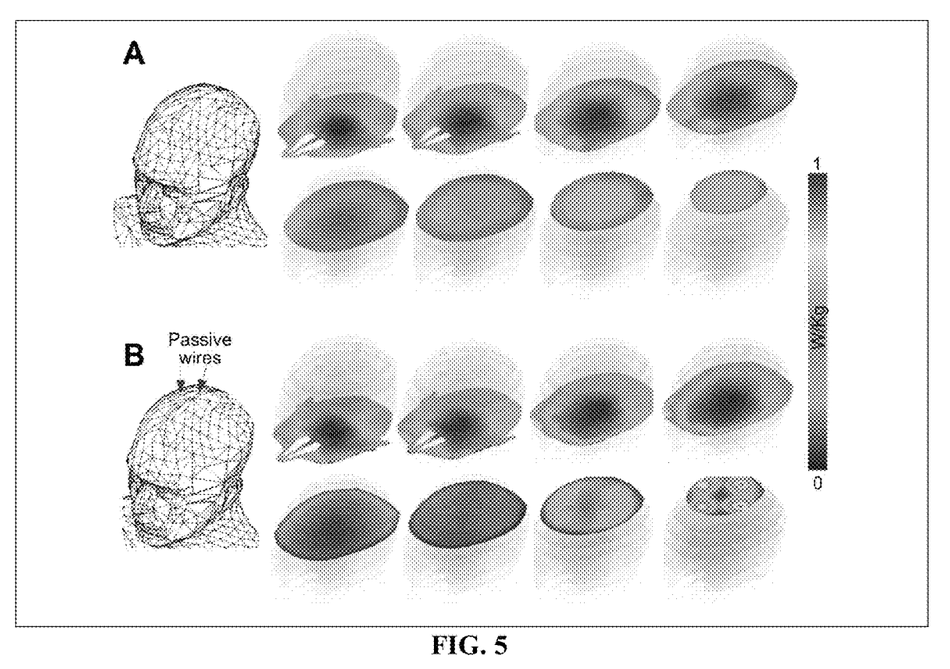
FIG. 5 is a diagram illustrating a slice-by-slice axial 10-gram specific absorption rate (SAR) maps, without (A) and with (B) a pair of wires placed very close (0.5 cm) to the top of the head.

A goal of the optimization will be to minimize the $B_1+$ coefficient of variation over the brain, subject to Specific Absorption Rate (SAR, measured in W/kg) constraints requiring that the maximum local (1-gram and 10-gram) and whole brain SAR in the brain does not violate FDA or IEC limits for a turbo spin-echo pulse sequence. An example of a 10-gram local SAR distribution is shown in FIG. 5. FIG. 5 shows a diagram illustrating slice-by-slice axial 10-gram specific absorption rate (SAR) maps, without (A) and with (B) a pair of wires placed very close (0.5 cm) from the top of the head. At this close spacing, the wires increase SAR in the topmost slice (lower right map of (B)). This optimization will ensure that any such increases remain within safety limits.

Design of a Mechanical Holder for the Wires, and a Method to Manufacture it by 3D Printing or other Suitable Processes.

Figure 6A:
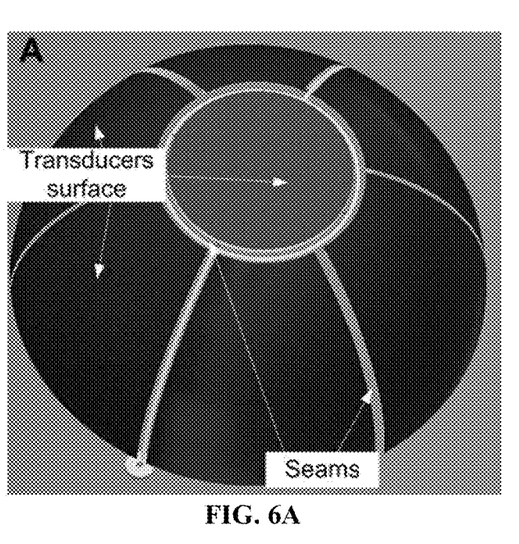
FIGS. 6A-6B are diagrams illustrating an exemplary holder for the passive crossed wires with the transducer surface (FIG. 6A) and without the transducer surface (FIG. 6B)
Figure 6B:
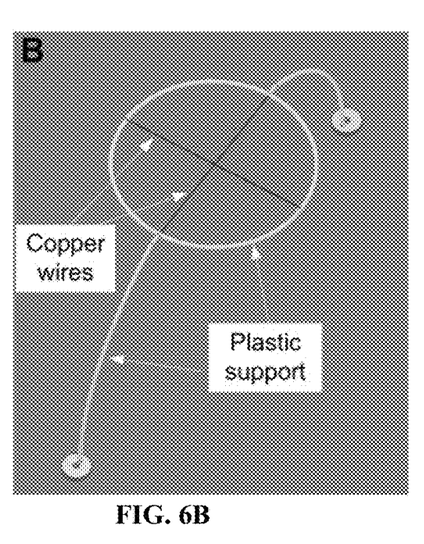

Mechanical Holder: One possible holder design for the wires is illustrated with the transducer surface (FIG. 6A) and without the transducer surface (FIG. 6B). The holder will be designed to suspend the wires in an optimal position as described above. The holder must provide robust and durable support for the wires, and have minimal effect on the ultrasonic waves. Considering those needs, the holder may have 2 or more legs (each of which is, for example, 1-4 mm thick) that reach down along, for example, the inner seams of the transducer as shown in FIG. 6A, to anchor it to the outer transducer rim, where it can be pinched against the transducer's outer rim by the ring of the membrane. The wires will run across the bath at a suitable height in accordance with the antenna optimization section above. As shown in FIG. 6B, the holder may incorporate a plastic ring around the transducer's upper ring-shaped seam to allow arbitrary wire rotations (see FIG. 6B). The wires may sit in the plane of the plastic ring of the support/holder as illustrated in FIG. 6B if that position is optimal, or the wires could drop down or rise up from it to the optimal height. The holder may be formed by, for example, 3D-printing using the VUIIS 3D Systems iPro 9000XL Printer.

The antenna may be affixed via, glue, to the plastic holder. The water circulates around and through the wires and the plastic holder. The wires are conductive and may be tin-coated copper, silver, or another electrically conductive material. An optional insulative coating such as a thin layer of Teflon® may be used. The wires are passive in that there is no electrical connection to them. The wires may be crossed (i.e., touching each other or separated from each other) or may be in other configurations. The wires may be planar or curved or bent in a non-planar manner. Multiple layers of wire may be employed. The wires may be crossed or in a pattern such as a "FIG.-8". The wires may instead be configured in a circle and may include multiple concentric circles that are not connected to each other. Each wire may be a single stranded or multi-stranded wire. There may be a single wire, two wires, or more than two wires. The wires may be placed centrally above the head or toward a side, front, or back portion of the head. The wires may each be thicker in diameter directly above the central part of the head and gradually be thinner moving further away from the central part. The wire thickness may be 12-28 gauge and preferably may be thinner than the wavelength of the ultrasound beam by a factor of at least 2.

Wires: High gauge tin-coated copper wires (>24 gauge/ <0.5 mm) may be used with the two ends of each wire pressed into the plastic holder. High-gauge RF wires in the path of a focused ultrasound (FUS) beam may be employed: Systems such as the Philips SonAlleve™ has built-in 0.5 mm-thick receive coil conductors embedded in the table's Mylar® window, directly in the middle of the beam path. This does not cause any significant disturbances to a >1 MHz acoustic field which has a shorter wavelength than the INSIGHTEC® brain systems, and sonication through the rod does not produce any noticeable artifacts in proton resonance frequency (PRF)-based temperature images. That same diameter is initially used, and if it causes FUS beam distortions a reduction in the diameter may be made until there are negligible distortions. The wires may be coated with thin insulation without compromising performance, though it is not believed to be necessary to ensure safety. Another alternative strategy would be to inject silver ink directly into hollow channels printed into the holder.

Figure 7:
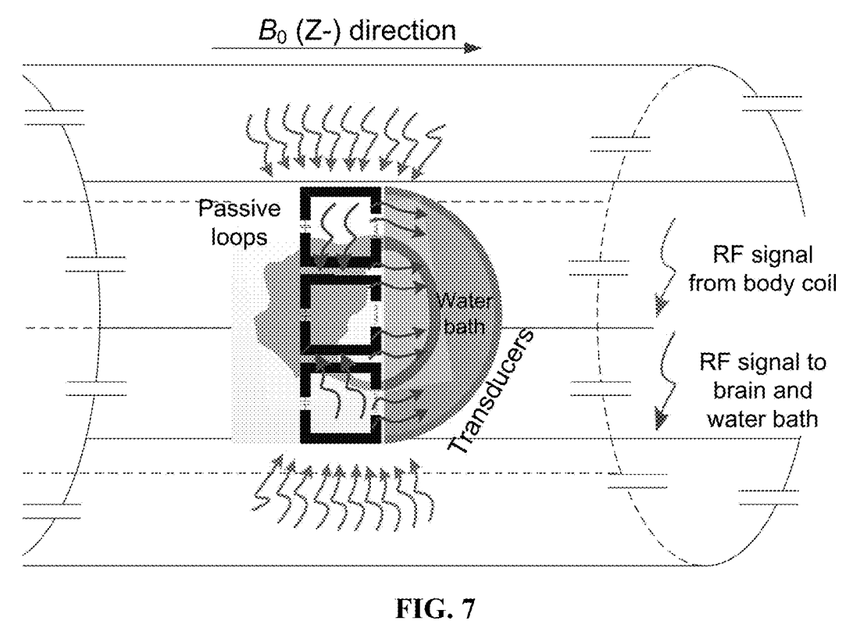
FIG. 7 is a diagram illustrating a ring of passive loops around a patient's head at the base of the transducer that may capture flux from the body coil and project it into the water bath.

As an alternative to the antenna/wires described above, a complementary ring of passive loop coils may instead be employed. The complementary ring will sit outside and below the transducer and could further increase the RF transmit and receive fields inside the head. FIG. 7 is a diagram illustrating the complementary ring of passive loops around a patient's head at the base of the transducer that may capture flux from the body coil and project it into the water bath, thereby further improving the $B_1$ efficiency both inside and outside the water bath. Like self-decoupled coils, the loops will have non-uniform impedance distributions around their circumference to achieve a higher current density near the water bath. Thus, like self-decoupled coils, they will behave as superimposed loops and folded dipoles. The loop modes will inductively couple to the body coil (i.e., pick up energy from it), and the dipole modes will project fields from the induced currents up into the water bath. The impedance distributions will be optimized to balance the two modes and achieve similar $B_1$ improvements inside and outside the water bath. Additionally, the loop positions, numbers, and sizes will be optimized. An optimal design may be mounted on an add-on cylindrical polycarbonic tube with a diameter of 35 cm. The tube may have no physical nor electrical connection thereto, so this tube could be floating. The tube could alternatively be screwed or otherwise affixed to the transducers bowl's outer frame to make the tube's position fixed. The loops will further improve the RF transmit and receive fields in the brain by a factor of at least 2.

Improvements in SNR and Transmit Efficiency and Validation that Hot Spots are not Distorted.

Image SNR and Transmit Efficiency: The wires are expected to increase image SNR by increasing the transmit efficiency which will increase flip angles in the brain, and also by increasing receive sensitivity. To evaluate these gains, time-series GRE images are collected in three planes in a healthy volunteer using a fast gradient-recalled echo (fGRE) pulse sequence used clinically for thermometry. The images are used to calculate through-time SNR as well as temperature precision with and without the wires and also with the water bath empty, to determine the amount of SNR recovered compared to the maximum possible. If a $B_1+$ mapping sequence is available, $B_1+$ maps will also be collected in these scenarios, to directly measure how much transmit efficiency is recovered compared to the maximum possible. Finally, T2-weighted turbo spin echo images and diffusion images will be collected in each scenario, to determine signal improvements for spin echo scans.

FUS Hot Spot Distortion: To check that the antennas do not distort the ultrasound beam, temperature maps are measured in three planes, in a hemispherical gel phantom using 15-30 seconds of acoustic heating targeting a temperature rise of at least 15 degrees Celsius. Each sonication will be repeated five times. The mean FWHM of the hot spot at peak heat (or the standard deviation of a Gaussian function fit to it) with and without the wires in the phase-encoded dimension of each scan are calculated and compared. No more than a 5% difference in the hot spot width or peak in any dimension is tolerated. As an alternative strategy, the beam could also be mapped outside the scanner with and without the wires using a hydrophone and motion stage.

In operation, MR-guided focused ultrasound therapy (e.g., non-invasive surgery) utilizes an ultrasound beam applied at a high-powered level such that tissue temperature is raised above about 60° C. to affect or kill tissue. For example, ablation of a portion of the hypothalamus for treating essential tremor (uncontrolled shaking of a portion of a patient's body) may benefit from using embodiments described herein. When performing the procedures, the patient's head is positioned inside a metal bowl transducer filled with water (e.g., tap water) or other fluid which is used to couple the acoustic energy from the transducer into the skull. The water is circulated between the sonications, i.e., between the temperature rises, in order to remove heat from the skull since the skull is highly absorptive of ultrasound energy. When the transducer is turned on, the MR device (which is used as a scanner) is simultaneously turned on to measure temperature, and the MR device is also used to perform diffusion imaging to localize the region that was just ablated because sometimes the temperature map doesn't effectively indicate whether the tissue is actually killed or not. The transmission of RF waves arising from a traveling wave coming up from the bottom of the transducer results in dark bands as described above. Thus, the therapeutic ultrasound techniques used in this disclosure may be for ablation. Alternatively, the therapeutic ultrasound techniques used in this disclosure may be for other therapies such as for opening the blood-brain barrier in order to deliver large-molecule drugs/therapies to the brain.

By placing an antenna into the water bath as described above, the phase and amplitude of the reflection can be controlled such that the reflection does not cancel with the incoming RF wave, and thus, the use of the passive antenna achieves reduction or elimination of the dark bands. The antenna controls the reflection obtained from the incoming wave such that it adds constructively with the incoming wave, thereby enhancing the image as if there was no water bath present.

Figure 8:
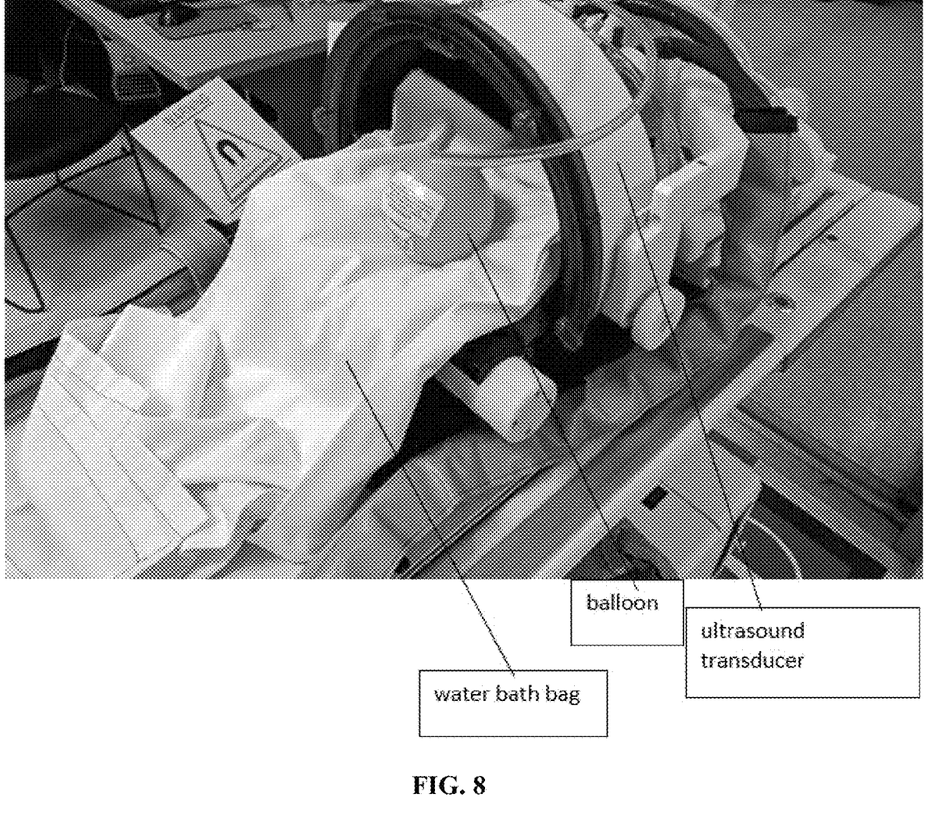
FIG. 8 is a diagram illustrating a transcranial ultrasound transducer and a water bath bag, along with a balloon representing a patient's head.

FIG. 8 shows a diagram illustrating a transcranial ultrasound transducer and a water bath bag, along with a balloon representing a patient's head. The balloon is outside the water bath bag for illustration purposes. For simplicity purposes, the antennas (i.e., to be positioned between the head/balloon and the transducer) and the MRI device are not shown.

As shown in FIG. 8, the rim of the transducer holds a water bath rubber membrane. The balloon is positioned where the heads goes, i.e., half inside the transducer and half outside the transducer. The natural focus of the transducer is in the middle of the balloon, where the brain structures to be destroyed or affected are positioned. The rubber membrane is positioned halfway down the patient's head and the opposite end clips into the rim of the transducer. The transducer is filled with water via the membrane. Water is circulated via tubes. The antenna goes inside the bath and is suspended in the bath by a plastic holder that runs along the inner seams of the transducer. The holder is fixed inside the transducer prior to the procedure, i.e., prior to the patient's head being positioned in the bath.

Figure 9:
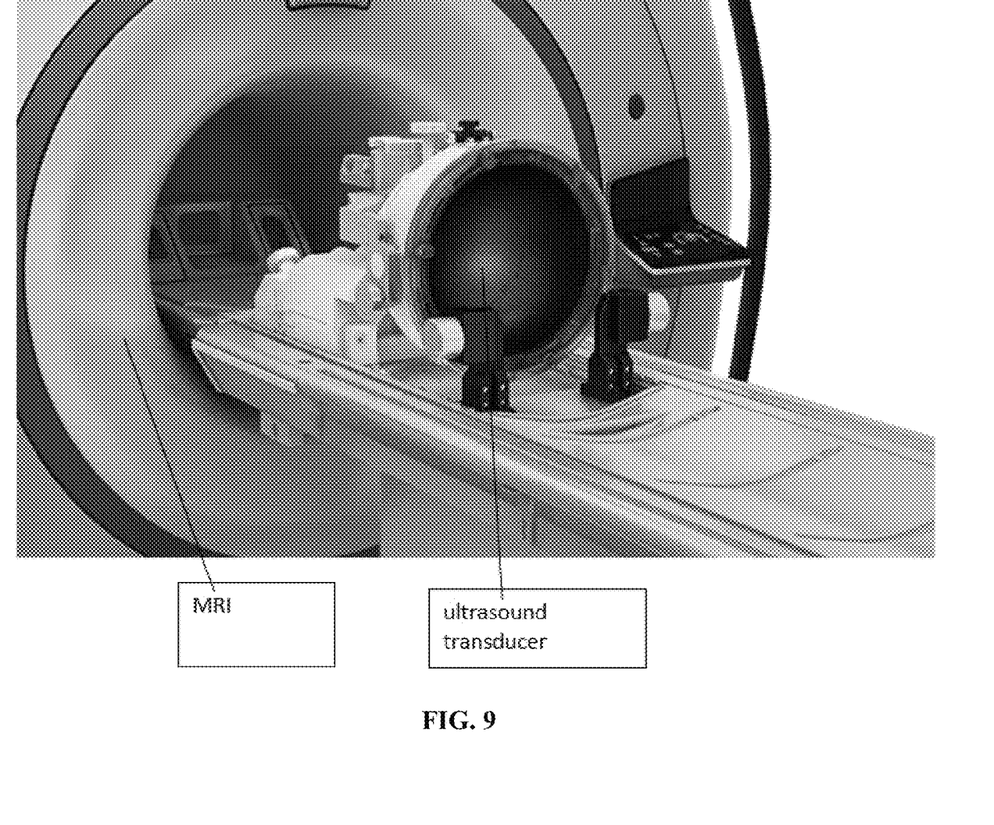
FIG. 9 is a diagram illustrating a transcranial ultrasound transducer and an MRI device.

FIG. 9 shows a diagram illustrating a transcranial ultrasound transducer and an MRI device.

Embodiments are directed to a system for transcranial MR-guided focused ultrasound. The system includes a transcranial ultrasound transducer configured to apply ultrasound radiation to a patient's head. The system also includes an antenna that reflects RF waves. The antenna is configured to be positioned between the transducer and the patient's head.

In an embodiment, the antenna and at least a portion of the patient's head are surrounded by a fluid. The fluid may be water. The antenna may be suspended in the fluid via a support operatively connected to the transducer.

In an embodiment, the antenna is passive such that there is no electrical connection thereto.

In an embodiment, the antenna includes two crossed wires.

In an embodiment, the antenna includes a configuration selected from the group consisting of at least one wire, two crossed wires, one wire in a "FIG.-8" pattern, one wire in a circle shape, two concentric non-connected circles, one multi-stranded wire, and a combination thereof.

In an embodiment, the system further includes an MR device configured to image the patient's head while the ultrasound radiation is applied to the patient's head. In one example, the reflected RF waves have not yet arrived at a surface of the transducer and have not been reflected at the surface of the transducer. In another example, the reflected RF waves do not cancel, affect, nor interfere with non-reflected RF waves in target areas such as within the head/brain, and serve to increase imaging sensitivity using the MR device.

Embodiments are also directed to a method of using transcranial MR-guided focused ultrasound. The method includes applying ultrasound radiation to a patient's head using a transcranial ultrasound transducer. The method also includes reflecting RF waves using an antenna positioned between the transducer and the patient's head.

In an embodiment of the method, the antenna and at least a portion of the patient's head are surrounded by a fluid. The fluid may be water. The antenna may be suspended in the fluid via a support operatively connected to the transducer.

In an embodiment of the method, the antenna is passive such that there is no electrical connection thereto.

In an embodiment of the method, the antenna includes two crossed wires.

In an embodiment of the method, the antenna includes a configuration selected from the group consisting of at least one wire, two crossed wires, one wire in a "FIG.-8" pattern, one wire in a circle shape, two concentric non-connected circles, one multi-stranded wire, and a combination thereof.

In an embodiment of the method, the method further includes imaging the patient's head using an MR device during the applying step. In one example, the reflected RF waves have not yet arrived at a surface of the transducer and have not been reflected at the surface of the transducer. In another example, the reflected RF waves do not cancel, affect, nor interfere with non-reflected RF waves in target areas such as within the head/brain, and serve to increase imaging sensitivity using the MR device.

This invention solves a major problem for transcranial MR-guided focused ultrasound, which is the very low MR image quality that results when the transducer is filled with a fluid such as water. This issue prevents the use of most clinical MR imaging scans when the transducer is filled, and especially the type of scans that would be helpful for monitoring treatment progress, such as diffusion MR.

The method steps in any of the embodiments described herein are not restricted to being performed in any particular order. Also, structures or systems mentioned in any of the method embodiments may utilize structures or systems mentioned in any of the device/system embodiments. Such structures or systems may be described in detail with respect to the device/system embodiments only but are applicable to any of the method embodiments.

Features in any of the embodiments described in this disclosure may be employed in combination with features in other embodiments described herein, such combinations are considered to be within the spirit and scope of the present invention.

The contemplated modifications and variations specifically mentioned in this disclosure are considered to be within the spirit and scope of the present invention.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A system for transcranial magnetic resonance (MR)-guided focused ultrasound, the system comprising:
   a transcranial ultrasound transducer configured to apply ultrasound radiation to a head of a patient, the transcranial ultrasound transducer comprising:
      a housing defining a cavity that is configured to receive the head of the patient; and
      a transducer surface within the housing;
   an antenna that is configured to reflect radio frequency (RF) waves; and
   a support configured to be connected to the transcranial ultrasound transducer and configured to suspend the antenna within the cavity, wherein: the support configured to support the antenna at a position at which,
   when the head is received within the cavity, the antenna is positioned entirely within the cavity between the housing and the head, and
   the antenna is passive and does not form an electrical connection.

2. The system of claim 1, wherein the antenna comprises two crossed wires.

3. The system of claim 1, wherein the antenna comprises one or more wires, the one or more wires being configured in at least one of a crossed pattern, a figure-eight pattern, a circular shape, a concentric, non-connected circular arrangement, or multiple strands.

4. The system of claim 1, further comprising a fluid surrounding the antenna and configured to surround the head when the head is received within the cavity.

5. The system of claim 4, wherein the fluid is water.

6. The system of claim 4, wherein the antenna is suspended in the fluid via the support.

7. The system of claim 1, further comprising an MR device configured to image the head while the ultrasound radiation is applied by the transcranial ultrasound transducer to the head.

8. The system of claim 7, wherein the MR device comprises a transmission coil that is configured to emit primary RF waves, and
when the primary RF waves are emitted from the transmission coil the antenna is configured to generate electrical currents that reflect secondary RF waves and to cause the secondary RF waves to propagate away from the antenna.

9. The system of claim 8, wherein the antenna and the transcranial ultrasound transducer are configured to combine the primary RF waves and the secondary RF waves inside the head to produce a total field for MR excitation.

10. The system of claim 9, wherein the MR device comprises an MR receiver coil that is configured to receive the primary RF waves from the head during signal reception by the MR device.

11. The system of claim 10, wherein
the antenna is configured to generate the secondary RF waves and to propagate the secondary RF waves away from the antenna when the primary RF waves are emitted from the head during the signal reception by the MR device, and
the MR device is configured to combine the primary RF waves and the secondary RF waves together in the MR device.

12. The system of claim 1, wherein
the housing is concave and comprises an inner surface,
the cavity comprises a bottom opening, and
the antenna is positioned within the cavity between the inner surface and the bottom opening and is configured to reflect RF waves entering the cavity from the bottom opening before the RF waves reach the inner surface.

13. The system of claim 12, wherein the support is connected to an outer rim of the transcranial ultrasound transducer and suspends the antenna within the cavity.

14. The system of claim 13, further comprising a fluid bath, wherein the fluid bath surrounds the antenna and is positioned within the cavity between the antenna and the inner surface.

15. A system for transcranial magnetic resonance (MR)-guided focused ultrasound, the system comprising:
a transcranial ultrasound transducer configured to apply ultrasound radiation to a head of a patient, the transcranial ultrasound transducer comprising:
a housing defining a cavity that is configured to receive the head of the patient; and
a transducer surface within the housing;
an antenna that is configured to reflect radio frequency (RF) waves; and
a support configured to be connected to the transcranial ultrasound transducer and configured to suspend the antenna within the cavity, wherein:
when the head of the patient is received within the cavity the antenna is between an inner surface of the housing and a top of the head, and
the antenna is passive and does not form an electrical connection.

16. The system of claim 15, further comprising an MR device configured to image the head while the ultrasound radiation is applied by the transcranial ultrasound transducer to the head.

17. The system of claim 15, wherein
the housing is concave,
the cavity comprises a bottom opening, and
the antenna is positioned within the cavity between the inner surface and the bottom opening and is configured to reflect RF waves entering the cavity from the bottom opening before the RF waves reach the inner surface.

18. A system for transcranial magnetic resonance (MR)-guided focused ultrasound, the system comprising:
a transcranial ultrasound transducer configured to apply ultrasound radiation to a head of a patient, the transcranial ultrasound transducer comprising:
a housing that is concave, the housing defining a cavity comprising a bottom opening that is configured to receive the head of the patient; and
a transducer surface within the housing;
an antenna that is configured to reflect radio frequency (RF) waves; and
a support configured to be connected to an outer rim of the transcranial ultrasound transducer and configured to suspend the antenna within the cavity, wherein:
when the head of the patient is received within the cavity the antenna is between an inner surface of the housing and a top of the head,
the antenna is passive and does not form an electrical connection, and
the antenna is positioned within the cavity between the inner surface and the bottom opening and is configured to reflect RF waves entering the cavity from the bottom opening before the RF waves reach the inner surface.

19. The system of claim 18, further comprising a fluid bath, wherein the fluid bath surrounds the antenna and is positioned within the cavity between the antenna and the inner surface.

20. The system of claim 19, wherein the fluid bath is a water bath.

\* \* \* \* \*